(12) United States Patent
Zhang et al.

(10) Patent No.: US 11,035,794 B2
(45) Date of Patent: Jun. 15, 2021

(54) SCALABLE, LARGE-AREA OPTICAL SENSING PLATFORM WITH COMPACT LIGHT DELIVERY AND IMAGING SYSTEM

(71) Applicants: UCHICAGO ARGONNE, LLC, Chicago, IL (US); THE UNIVERSITY OF CHICAGO, Chicago, IL (US); THE MARING BIOLOGICAL LABORATORY, Woods Hole, MA (US)

(72) Inventors: Xufeng Zhang, Westmont, IL (US); Supratik Guha, Chicago, IL (US); Zoe G. Cardon, Falmouth, MA (US)

(73) Assignees: UCHICAGO ARGONNE, LLC, Chicago, IL (US); THE UNIVERSITY OF CHICAGO, Chicago, IL (US); THE MARINE BIOLOGICAL LABORATORY, Woods Hole, MA (US)

( * ) Notice: Subject to any disclaimer, the term of this patent is extended or adjusted under 35 U.S.C. 154(b) by 82 days.

(21) Appl. No.: 16/146,360

(22) Filed: Sep. 28, 2018

(65) Prior Publication Data
US 2020/0103346 A1    Apr. 2, 2020

(51) Int. Cl.
*G01N 21/64* (2006.01)
*C12Q 1/6874* (2018.01)

(52) U.S. Cl.
CPC ....... *G01N 21/6428* (2013.01); *C12Q 1/6874* (2013.01); *G01N 21/645* (2013.01);
(Continued)

(58) Field of Classification Search
CPC .......... G01N 21/6428; G01N 21/6408; G01N 21/645; G01N 2021/6434;
(Continued)

(56) References Cited

U.S. PATENT DOCUMENTS 7,702,381 B2    4/2010 Gaeta et al.
8,269,261 B2    9/2012 Rothberg et al.
(Continued)

FOREIGN PATENT DOCUMENTS

WO    WO-2017123296 A1 *  7/2017  ............. G01N 21/78
WO    WO-2018/069358 A1   4/2018

OTHER PUBLICATIONS

Lapresta-Fernandez, A., and L. F. Capitán-Vallvey. "Evaluation of analytical reflection scanometry as an analytical tool." Analytical Methods 3.11 (2011): 2644-2650. (Year: 2011).*
(Continued)

*Primary Examiner* — Robert J Eom
(74) *Attorney, Agent, or Firm* — Marshall, Gerstein & Borun LLP

(57) ABSTRACT

An optode has a planar radiation guiding medium having a first planar surface and a second planar surface and one or more perimeter surfaces bounded by the first and second planar surfaces. An excitation energy source of the optode is configured to output into the radiation guiding medium first energy at a wavelength selected to excite a fluorophore. The optode also includes a photodetector configured to image at least a portion of the first planar surface of the radiation (Continued)

guiding medium by detecting second energy transmitted through the radiation guiding medium.

20 Claims, 9 Drawing Sheets

(52) U.S. Cl.
CPC . *G01N 21/6408* (2013.01); *G01N 2021/6434* (2013.01); *G01N 2021/6439* (2013.01); *G01N 2021/6463* (2013.01); *G01N 2201/062* (2013.01); *G01N 2201/126* (2013.01)

(58) Field of Classification Search
CPC ... G01N 2021/6439; G01N 2021/6463; G01N 2201/062; G01N 2201/126; C12Q 1/6874
See application file for complete search history.

(56) References Cited

U.S. PATENT DOCUMENTS

| | | |
|---|---|---|
| 9,075,225 B2 | 7/2015 | Fine |
| 2013/0244266 A1 | 9/2013 | Reardon et al. |

OTHER PUBLICATIONS

Papageorgiou, Efthymios P., et al. "Real-time cancer detection with an integrated lensless fluorescence contact imager." Biomedical Optics Express 9.8 (2018): 3607-3623. (Year: 2018).*

Askim, Jon Robert. Portable colorimetric sensor array technology. Diss. University of Illinois at Urbana-Champaign, 2015. (Year: 2015).*

Vaknin et al., "Single-Cell FRET Imaging of Phosphatase Activity in the *Excherichia coli* Chemotaxis System," *PNAS*, vol. 101, No. 49 (2004).

Cortesi et al., "Reliable measurement of *E. coli* single cell fluorescence distribution using a standard microscope set-up," *Journal of Biological Engineering* (2018).

Sandeau et al., "Large area CMOS bio-pixel array for compact high sensitive multiplex biosensing," *Lab on a Chip* (2015).

Tengberg et al., "Evaluation of a lifetime-based optode to measure oxygten in aquatic systems," *Limnology and Oceanography: Methods*, (2006).

Suma et al., "Nanotechnology Enaled *E.coli* Sensors: An Opto-Electronic Study," *Materials Today: Proceedings*, (2017).

* cited by examiner

SCALABLE, LARGE-AREA OPTICAL SENSING PLATFORM WITH COMPACT LIGHT DELIVERY AND IMAGING SYSTEM

STATEMENT REGARDING FEDERALLY SPONSORED RESEARCH OR DEVELOPMENT

This invention was made with government support under Contract No. DE-AC02-06CH11357 awarded by the United States Department of Energy to UChicago Argonne, LLC, operator of Argonne National Laboratory. The government has certain rights in the invention.

FIELD OF THE DISCLOSURE

The present disclosure relates to sensing devices used for determining the presence and/or concentration of analytes, and, in particular, to a compact optical biochemical sensing platform.

BACKGROUND

Real-time chemical analysis of a field sample is important for applications such as water and air pollution measurements, monitoring chemical composition of soils, and biomedical testing. Tracking analyte movement over a region can also be required in some measurements to show how an environment changes over time.

Biochemical-sensing optical imaging systems (sometimes referred to as optodes) can measure optical signals to determine the presence and concentration of an analyte in a sample, typically using an intermediary chemical transducer. In particular, the optical signal is typically a fluorescent signal, and the chemical transducer is typically a fluorophore, that generates a fluorescent signal modulated by the presence or concentration of the analyte in question. For example, where the analyte in question is humidity, a humidity-sensitive fluorophore may be exposed to the environment in question. Upon binding with (or otherwise interacting with) the fluorophore, the fluorophore may fluoresce, generating the optical signal. As is well-understood, some fluorophores require the excitation energy—perhaps at a specific wavelength—in order for the fluorophore to fluoresce when exposed to the analyte. The analyte may affect the fluorescence of a fluorophore in various ways including altering the intensity of the fluorescence, the lifetime or how long the fluorophore fluoresces, and phase shift of the fluorescence. The presence and/or concentration of an analyte may be determined using any of the affected characteristics of a fluorophore.

FIG. 1 illustrates a traditional optode embodiment 100. As shown in FIG. 1, an excitation energy source 102 emits excitation energy 118 toward a sample 104 to cause a fluorophore in, or in contact with, the sample 104 to emit secondary energy 108 (e.g., fluorescence). The interaction of an analyte in the sample 104 with the fluorophore may change how much the fluorophore fluoresces. A camera 106 positioned in the optical path of the secondary energy 108 receives and/or records the secondary energy 108 as image information. A computer 110 communicatively coupled to and receiving the image information from the camera 106 processes the image information to determine from the secondary radiation 108 (i.e., from the presence, intensity, and/or distribution of the fluorescence) the presence, concentration, and/or distribution of an analyte in the sample 104. Commonly, optodes employ an SLR (single-lens reflex) camera having a (sometimes substantial) lens 120 to detect and record the secondary radiation 108, and LEDs with guidance mirrors or fiber bundles as the excitation energy source 102. Optical filters 114, 116 are commonly used to limit the wavelengths of the excitation energy 118 to those required for the fluorophore and to limit the wavelengths of the secondary radiation 108 to those of the signal of interest. Implementations of optodes that use such bulky components require disturbing the environment around the optode. Additionally, the excitation energy and optical signal must traverse multiple material interfaces (e.g., glass/air, etc.) and generally travel through open air for some distance between the sample 104 and the camera 106 and/or excitation energy source 102, which can introduce distortions that render the optode output data less accurate.

SUMMARY OF THE DISCLOSURE

An optode includes a planar radiation guiding medium having a first planar surface and a second planar surface and one or more perimeter surfaces bounded by the first and second planar surfaces, an excitation energy source configured to output into the radiation guiding medium first energy at a wavelength selected to excite a fluorophore, and a photodetector configured to image at least a portion of the first planar surface of the radiation guiding medium by detecting second energy transmitted through the radiation guiding medium.

A system includes a planar radiation guiding medium having a first planar surface and a second planar surface and one or more perimeter surfaces bounded by the first and second planar surfaces, an excitation energy source configured to output into the radiation guiding medium first energy at a wavelength selected to excite a fluorophore, and a photodetector configured to image at least a portion of the first planar surface of the radiation guiding medium by detecting second energy transmitted through the radiation guiding medium. The system also includes a processor communicatively coupled to the photodetector and configured to receive from the photodetector a signal representing the detected second energy and to analyze the received signal to determine the presence and/or concentration of an analyte.

DETAILED DESCRIPTION

Figure 1:
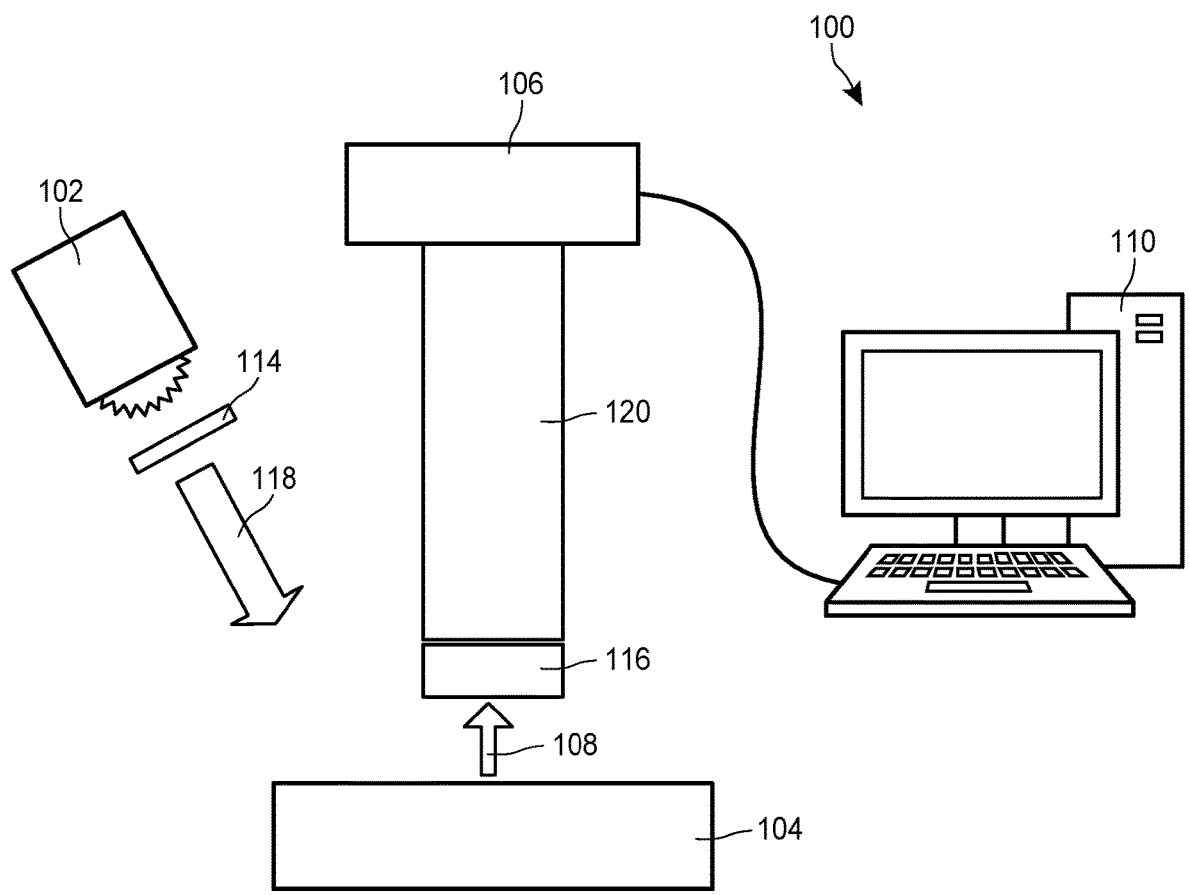
FIG. 1 illustrates a typical embodiment of an optode system according to the prior art.

An optode in accordance with the present description generally features a compact design compared to other optode technologies. The optode employs a generally planar radiation guiding medium to deliver excitation radiation to a sample. Small form-factor detectors with short focal distances are used to image a region to detect the presence and/or concentration of an analyte.

The devices and methods described result in a scalable, optical sensing platform with compact light delivery, detection, and imaging. The scalability of the platform is suitable, in embodiments, to sensing over relatively large areas (e.g., up to square meters). The ability to image large areas allows for high sensitivity measurements of low concentrations of biological or chemical targets. The compact design of the devices and methods described provide benefits for environmental sensing such as simpler installation schemes and reduced impact on the surrounding environment.

In electromagnetics, it is common to distinguish a frequency, wavelength, energy, and color of electromagnetic radiation. Each of these four characteristics is related to the other three. For example, the wavelength, in nanometers (nm), and frequency, in hertz (Hz), for a specified electromagnetic radiation are inversely proportional to each other. The product of the frequency and wavelength for a given electromagnetic radiation is equal to the speed of light. Therefore, higher frequencies correspond to shorter wavelengths, and conversely, lower frequencies correspond to longer wavelengths for a given electromagnetic radiation. Similarly, the energy, in electron-volts (eV) or joules (J), of electromagnetic radiation is proportional to the frequency by a constant known as Planck's constant. Therefore, for a given radiation at a given frequency, there is a corresponding wavelength and energy. Similarly, for a given radiation with a given wavelength, there is a corresponding frequency and energy. The same goes for a given radiation with a given energy, there is a corresponding frequency and wavelength.

The fourth of the aforementioned characteristics, color, typically represents a group or band of frequencies or wavelengths. For example, the color blue is commonly defined as electromagnetic radiation with a wavelength from 450 nm to 495 nm. This wavelength band also corresponds to frequencies from 606 THz to 668 THz, and energies of 2.5 to 2.75 eV. The color blue, is then, any radiation with one of those wavelengths, or radiation with multiple wavelengths in that band. Therefore the term color may refer to one specific wavelength, or a band of wavelengths. Some areas of trade in electromagnetics prefer the use of one of the four terms over the others (e.g. color and wavelength are preferred when discussing optical filters, whereas frequency and energy are preferred when discussing fluorescent processes). Therefore, the four terms may be understood to be freely interchangeable in the following discussion of electromagnetic radiation and an optode device.

An optode according to the present description employs a radiation guiding medium to deliver excitation energy to a fluorophore. The fluorophore may be affected by an analyte which alters a characteristic of a fluorescent process of the fluorophore, or it can be specifically bound to the analyte. The analyte may be any analyte that interacts with a fluorophore to produce an optical signal. By way of example, analytes may include gaseous oxygen ($O_2$), gaseous carbon dioxide ($CO_2$), acidity, deoxyribonucleic acid (DNA), ribonucleic acid (RNA), an organic molecule, an inorganic molecule, or a pathogen. Some characteristics of a fluorophore may include, without limitation, fluorescence intensity, fluorescence decay time, and fluorescence wavelength. Embodiments implementing a fluorophore may utilize multiple radiations, e.g. a reference radiation and target signal radiation as described further below. Utilizing a reference radiation may improve the accuracy of measuring the presence and/or concentration of an analyte, which is discussed further below.

Figure 2A:
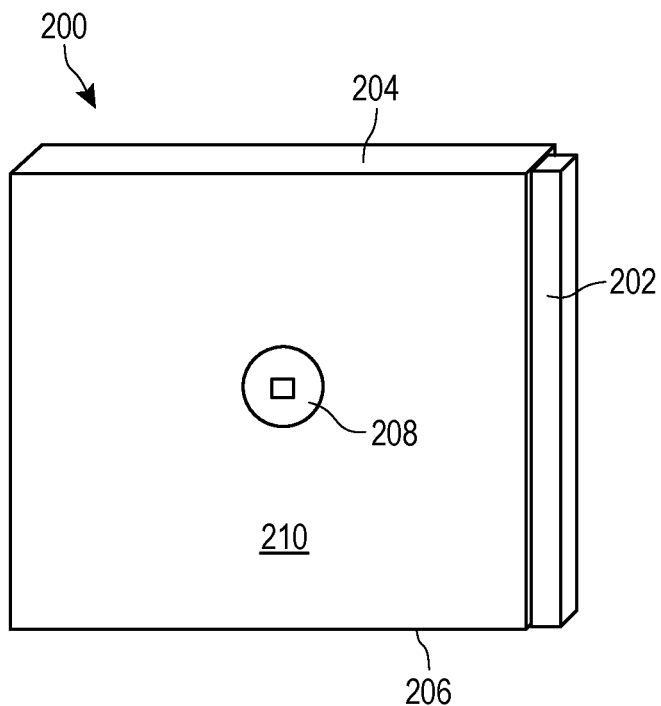
FIGS. 2A and 2B are front and rear views, respectively, of an embodiment of a compact optode with a planar radiation guiding medium, excitation source, and a photodetector.
Figure 2B:
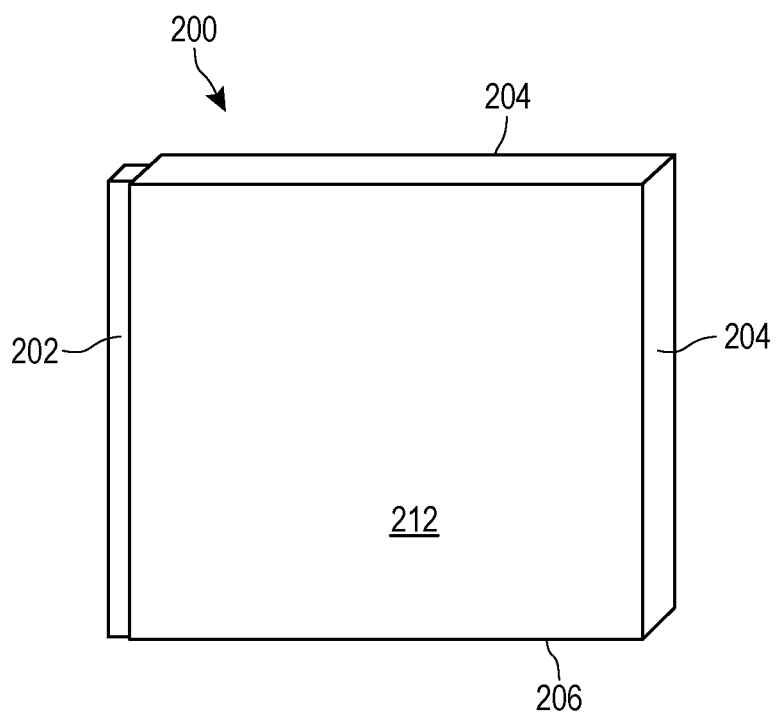

FIGS. 2A and 2B are front and rear views, respectively, of an embodiment of a compact optode 200. In the embodiment of the optode 200 depicted in FIGS. 2A and 2B, and in fact, in most contemplated embodiments, a generally planar radiation guiding medium 206 guides excitation energy in the form of electromagnetic radiation from an excitation energy source 202 and delivers it to a fluorophore, analyte, or sample. The generally planar radiation guiding medium 206 includes a first planar surface 210 a second planar surface 212 and one or more perimeter surfaces 204 (e.g., for the rectangular medium 206, there are four perimeter surfaces 204). The radiation guiding medium 206 need not be perfectly planar and may be curved as long as the radiation guiding medium 206 is able to guide radiation from an excitation energy source 202 to a fluorophore, analyte, or sample.

A radiation guiding medium 206 is a material designed in composition and shape to manipulate the path of optical radiation. Such a radiation guiding medium 206 is able to guide radiation along one or more dimensions of the medium 206 by means of total internal reflection. While common examples of radiation guiding mediums 206 are dielectric waveguides such as optical fibers, metal waveguides such as transmission lines, and semiconductor waveguides such as silicon-on-insulator waveguides, the radiation guiding mediums 206 described throughout this specification are generally planar and are selected to guide optical radiation. Depending on the frequency, environment, and application of the radiation being guided, the radiation guiding medium 206 may be a polymer such as plastics, glass such as silica, semiconductor such as silicon, other material such as lithium niobate or potassium titanyl phosphate, or any other material able to guide optical radiation as required by the present application or system.

Figure 3A:
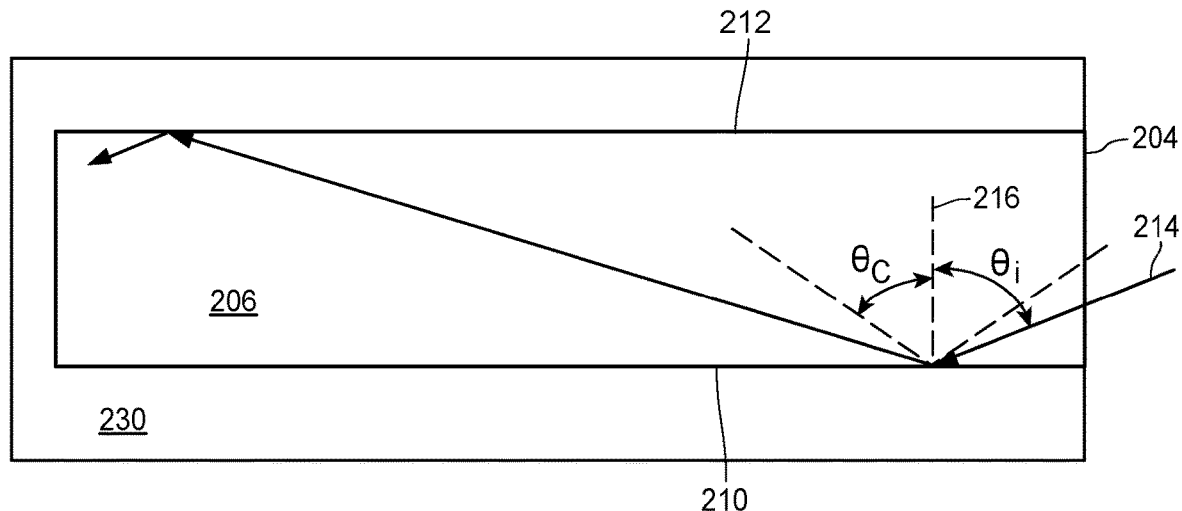
FIGS. 3A and 3B illustrate the physical phenomena of total internal reflection in a radiation guiding medium of the present description.

Although radiation guiding mediums 206 may be comprised of any number of materials, geometries, and/or shapes, the radiation guiding medium 206 of the optode 200 of FIGS. 2A and 2B will be used in further discussion for simplicity and clarity. FIG. 3A illustrates radiation 214 entering a radiation guiding medium 206 through a perimeter surface 204. The planar surfaces 210 and 212 totally internally reflect the radiation 214 in the radiation guiding medium 206. The radiation guiding medium 206 may be comprised of plastic, water, doped silica, a first type of glass, or any other material provided that the conditions for total internal reflection at the interfaces of the planar surfaces 210 and 212 are met. The environment or non-guiding medium 230 at the interfaces of the planar surfaces 210 and 212 may be air (as illustrated in FIGS. 2A and 2B), water, metal, doped silica, a second glass, or any other material provided that the conditions for total internal reflection at the interfaces of the planar surfaces 210 and 212 are met.

To achieve total internal reflection at the interfaces of the planar surfaces 210 and 212 and the non-guiding medium 230, the index of refraction of the environment or non-guiding medium 230 must be less than the index of refraction of the radiation guiding medium 210. The specific values of the indices of refraction of the radiation guiding medium 206 and the non-guiding medium 230 determine a critical angle, $\theta_C$, the critical angle $\theta_C$ being relative to a normal axis 216 orthogonal to the planar surfaces 210 and 212. The radiation 214 is incident on the first planar surface 210 at an angle of incidence, $\theta_i$ relative to the normal axis 216. In FIG. 3A, the angle of incidence $\theta_i$ is greater than the critical angle $\theta_C$ of the radiation guiding medium 206. The radiation guiding medium 206 totally internally reflects the radiation 214 incident on either of the planar surfaces 210 and 212 at angles of incidence $\theta_i$ greater than the critical angle $\theta_C$.

Figure 3B:
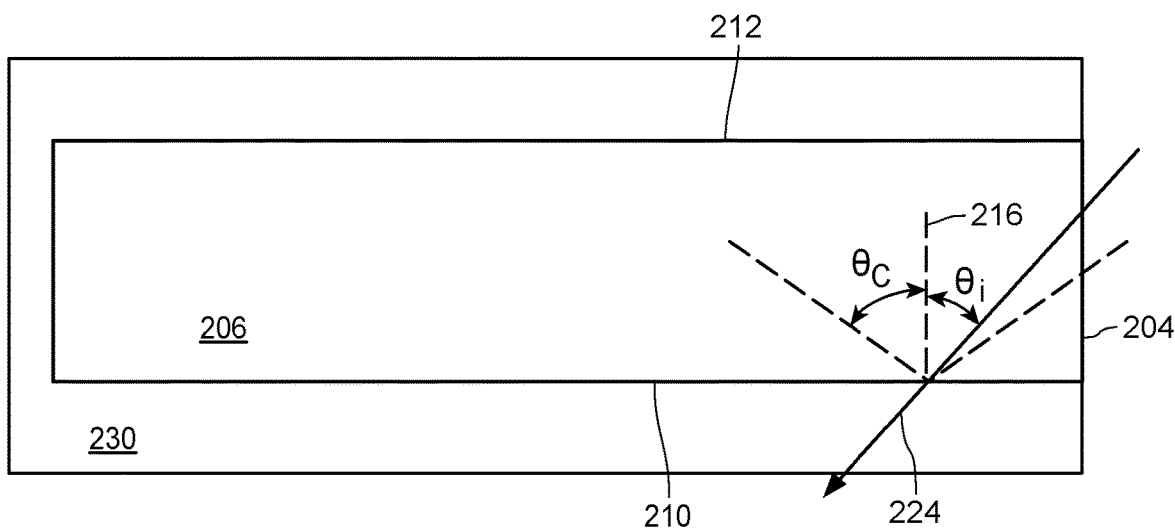

FIG. 3B illustrates a scenario where radiation 224 is incident on the first planar surface 210 of a radiation guiding medium 206 at an angle of incidence $\theta_i$ less than the critical angle $\theta_C$ of the radiation guiding medium 210. In FIG. 3B the radiation 224 passes through the first planar surface 210 of the radiation guiding medium 250 into the non-guiding medium 230 and is therefore not totally internally reflected.

In addition to the index of refraction, other factors impact what material the radiation guiding medium should be for a given embodiment. In some embodiments, specific frequencies, or energies, of electromagnetic radiation may be required to excite one or more fluorophores, therefore the radiation guiding medium 206 should be transparent at the frequencies of the excitation energy. In embodiments, reference and/or signal radiation may also need to pass through the radiation guiding medium 206, potentially from fluorophore to a photodetector. In such embodiments the radiation guiding medium 206 should also be transparent to energies at reference and signal frequencies or energies.

Although the radiation guiding medium 206 described herein is deemed planar, the medium 206 is not a two dimensional plane, but in fact a three dimensional object. The radiation guiding medium 206 has a height, a width, and a depth where two of the three dimensions are of equal or greater size than the third dimension. The two dimensions of equal or greater size than the third dimension constitute the dimensions of the planar surfaces 210 and 212 of the radiation guiding medium 206. Therefore, the planar radiation guiding medium 206 may be a cube, or a hyperrectangle (a rectangular box). Again, the radiation guiding medium 206 need not be perfectly planar and may have a curvature along any of the radiation guiding medium's 206 three dimensions. In fact, any the of surfaces of the radiation guiding medium 206 may have similar or different curvatures provided that the radiation guiding medium 206 is able to totally internally reflect electromagnetic radiation at the frequencies of interest (e.g. the excitation energy).

The radiation being guided by the radiation guiding medium 206 may be excitation energy provided by an excitation energy source 202. An excitation energy source 202 is, in embodiments, attached to one or more of the perimeter surfaces 204 of the planar radiation guiding medium 206. In embodiments the excitation energy source 202 may be embedded into the radiation guiding medium 206 at a perimeter surface 204 of the radiation guiding medium 206. The excitation energy sources 202 could also be attached to the radiation guiding medium 206 using conventional adhesive tapes, glues, hook and loop fasteners (e.g. Velcro), clips, or any other method able to position the excitation energy source 202 such that it injects excitation energy into the radiation guiding medium 206.

In other embodiments, a carriage structure may be attached to the perimeter surfaces 204 of the radiation guiding medium 206. The carriage structure being designed to hold the excitation energy source 202 in place. Such a carriage structure would allow for excitation energy sources 202 to be modular, and therefore easily removed from or interchanged on the optode 200. A new excitation energy source 202 may then be installed therefore potentially simplifying maintenance and increasing the optode's 200 lifetime. Due to different excitation energy requirements of various fluorescent processes, ease of interchanging modular excitation energy sources 202 may provide a simple way of changing an optode's 200 target analyte. For example changing the excitation energy source 202 to a different excitation energy source 202 that emits a different excitation energy may allow an optode 200 to switch from detecting the presence and/or concentration of a first substance in a sample, to measuring another substance of that same sample or any other sample. In embodiments, simple replacement of modular optode components such as excitation energy sources 202, photodetectors 208, protective panels (discussed further below), and any other components may be desirable. Simple interchanging of modular optode components could prevent further disturbing the surrounding environment, simplify optode maintenance, and increase versatility of optode analyte measurements.

While the embodiment of the optode 200 shown in FIGS. 2A and 2B employs only one excitation energy source 202, other embodiments may have more than one excitation energy source 202 positioned to inject excitation energy into a radiation guiding medium 206 along multiple perimeter surfaces 204. In addition, excitation energy sources 202 need not cover the entire perimeter surfaces 204, permitting that enough excitation energy is delivered to a sample or fluorophore to allow the optode 200 to determine the presence and/or concentration of an analyte.

In any embodiment, the excitation energy sources 202 may be light emitting diodes, lasers, black body radiation sources, high-intensity discharge lamps, or any other current or future excitation energy source 202 able to provide excitation energy adequate to cause a fluorophore or analyte (and in particular the desired fluorophore or analyte) to fluoresce. The excitation energy sources 202 should be one that provides excitation energy at energy levels high enough to excite the selected fluorophore, and broadband enough to excite all of the fluorescent processes of interest in a given embodiment. The excitation energy sources 202 may also provide excitation energy in a continuous or pulsed manner depending on the frequencies of the fluorescent processes, fluorescence lifetime, fluorophore susceptibility to photobleaching, potential optical filtering, photodetector speed or response time, and/or other factors.

In any embodiment the excitation energy sources 202 may be single sources or small groups of sources. Excitation energy sources 202 may be arranged as one dimensional arrays with dimensions of 1 by N where N is the number of excitation energy sources 202. Excitation energy sources 202 may be arranged as two dimensional arrays with dimensions of 2 by N where the number of excitation energy sources 202 is twice the value of N. The excitation energy sources 202 may be arranged as any spatial pattern or configuration such that the excitation energy is relatively evenly distributed to a fluorophore or analyte, and/or enough excitation energy is delivered to a fluorophore or analyte adequate to cause a fluorophore or analyte to fluoresce. The spatial configuration of the excitation sources 202 may depend on the means by which the radiation guiding medium 206 emits the excitation energy from the radiation guiding medium 206. Factors to consider when choosing an excitation energy source 202 for a given embodiment include, without limitation, the frequency or energy of the excitation energy required for the fluorescent processes of interest, output luminance, heat dissipation, form factor including dimensions of the excitation energy sources 202, form factor including dimensions of the radiation guiding medium 206, radiation losses due to the radiation guiding medium 206, the sensitivities and efficiencies of one or more photodetectors 208, and the complexity of the electrical connections to the excitation energy sources 202.

In embodiments, the excitation energy source 202 may be configured as one or more light emitting diodes (LEDs) disposed along perimeter surfaces 204 of the planar radiation guiding medium 206. In other embodiments, such as that illustrated in FIG. 5A, the excitation energy source 202 may be an array 402 of individual excitation energy sources disposed on or near the first planar surface 210 of the planar radiation guiding medium 206. The embodiment 400 of FIG. 5A may provide excitation energy to a fluorophore or analyte without utilizing total internal reflection. The excitation energy source array 402 directs excitation energy through the planar surfaces 210 and 212 of the radiation guiding medium 206, directly into a fluorophore or analyte at our near the opposing surface 212 of the radiation guiding medium 206. Although the embodiment 400 depicted in FIG. 5A may not employ a radiation guiding medium 206, the embodiment 400 of FIG. 5A introduces more complexity in arranging and supplying power to the excitation energy source array 402. The embodiment 400 depicted in FIG. 5A could also increase the thickness of the optode device, and the excitation energy source array 402 could provide less evenly distributed excitation energy to a target area or region. Although, an embodiment with an excitation energy source array 402 could facilitate pixel by pixel control of the device and could allow for illumination of target areas or regions of interest, potentially increasing the lifetime of a given fluorophore as described below.

In the embodiment of the optode 200 of FIGS. 2A and 2B, a photodetector 208, disposed on or adjacent to the first planar surface 210, is configured to image the opposing planar surface (e.g., the second planar surface 212) of the radiation guiding medium 206. As used herein, the term photodetector, unless otherwise indicated in a specific embodiment, generally refers to any device or array of devices configured to detect an optical signal. In operation, the optode 200 is disposed such that the analyte of interest is in contact with the opposing planar surface 212 or in contact with a protective panel on the opposing planar surface 212, being imaged by or within the focal distance of the photodetector 208. In such an embodiment of the compact planar optode 200, the form factor of the device, including its dimensions, is defined by the radiation guiding medium 206 and not by the photodetectors 208 and excitation energy sources 202.

Figure 4A:
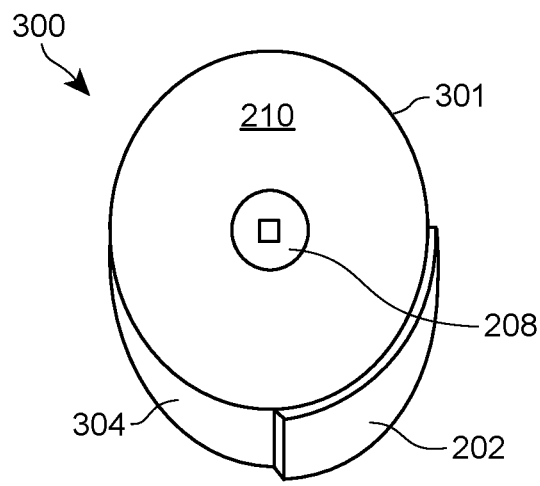
FIGS. 4A-4C depict various embodiments of a compact optode having different shaped planar radiation guiding mediums, multiple excitation sources, and a photodetector.
Figure 4B:
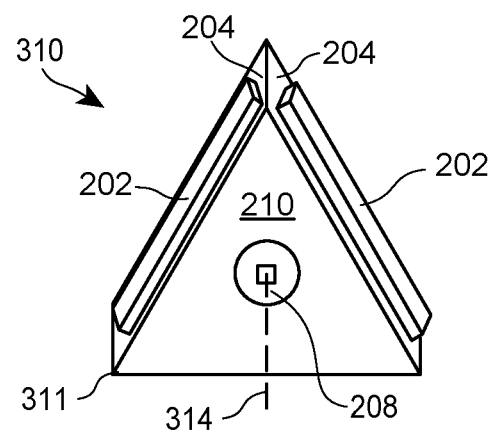
Figure 4C:
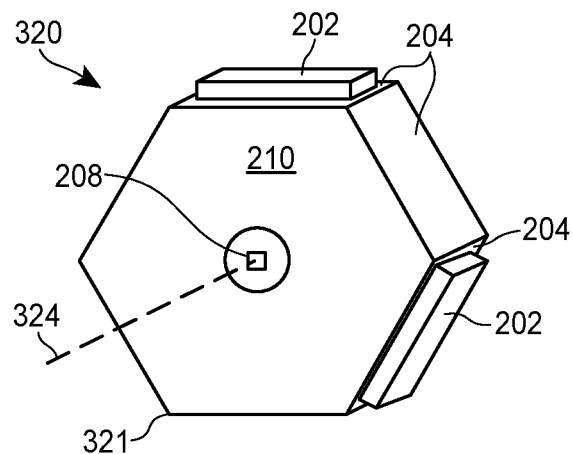

While depicted in FIGS. 2A and 2B as rectangular, the planar radiation guiding medium 206 need not necessarily be rectangular. FIG. 4A illustrates an embodiment of a compact optode 300 employing a circular planar radiation guiding medium 301. An excitation energy source 202 injects excitation energy into the circular radiation guiding medium 301 through a perimeter surface 304. A photodetector 208 disposed on or adjacent a first planar surface 210 of the circular planar radiation guiding medium 301 is configured to image the opposing planar surface 212 of the radiation guiding medium 301. FIGS. 4B and 4C illustrate embodiments 310 and 320, respectively, in which the planar radiation guiding medium 311 and 312, respectively, is triangular and hexagonal. One or more excitation energy sources 202 may be arranged to inject excitation energy into the planar radiation guiding mediums 311 and 321 at one or more corresponding perimeter surfaces 204 of the planar radiation guiding mediums 311 and 321. The use of multiple excitation energy sources 202 may allow for more even distribution of excitation energy delivered to the fluorophore, sample, or analyte, depending on the geometry of the planar radiation guiding mediums 311 and 321 and sample being analyzed. In embodiments, the distribution of excitation energy sources 202 is symmetrical about axes 314 and 324 orthogonal to the planar surfaces 210 and 212 of the planar radiation guiding mediums 311 and 321.

Like the embodiments 200 and 400 depicted in FIGS. 2A, 2B, and 4A the embodiments in FIGS. 4B and 4C also employ photodetectors 208 disposed on the first planar surfaces 210 of the planar radiation guiding mediums 311 and 321. The photodetectors 208 are configured to image the opposing planar surfaces 212, respectively, of the planar radiation guiding mediums 311 and 321.

As is understood, photodetectors 208 detect the intensity of electromagnetic radiation. Photodetectors 208 can be designed to detect different electromagnetic radiation frequencies, or energies. Some photodetectors 208 detect many frequencies, or a wide band of frequencies, while other photodetectors 208 detect few frequencies, or narrow bands of frequencies, of electromagnetic radiation. The frequency of the electromagnetic radiation determines its color and energy. Photodetectors 208 that detect a narrow band of frequencies may be employed to discern the color or energy of electromagnetic radiation. Alternatively, wide frequency-band photodetectors 208 with narrow-band color filters may also be implemented to discern the color or energy of electromagnetic radiation. In some embodiments, multiple narrow-band photodetectors 208, detecting different frequency bands, may detect fluorescent energies at different colors or frequencies. Such an embodiment enables multiple fluorescent processes to be observed simultaneously, allowing multiple analytes to be analyzed, and/or one or more reference and signal fluorescent processes to be observed. In other embodiments, one or more wide-band photodetectors 208, detecting the same frequency band, may detect multiple colors or frequencies, and a processor may perform filtering and analysis of digital data to determine the presence and/or concentration of an analyte or multiple analytes. The processor may also analyze a reference signal to increase the accuracy of the measurement of a target analyte or analytes, as described below.

Figure 5A:
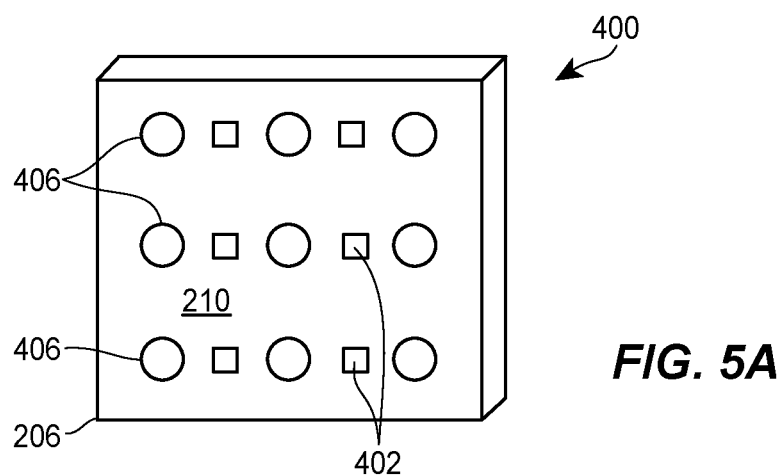
FIG. 5A depicts an embodiment of a compact optode in which photodetectors and excitation energy sources are disposed on a planar surface of the radiation guiding medium.

Photodetectors 208, without lenses, may have wide fields of view which means the photodetectors 208 accept radiation from many directions at once. Such a photodetector 208 does not generally allow one to discern what point or region in space detected electromagnetic radiation propagated from, reducing or eliminating image information. A single photodetector 208 comprising a single pixel, such as a single photodiode, thereby provides very low spatial resolution or image information as the single pixel may represent a large region of space. By altering the field of view of a photodetector 208, the photodetector 208 may be used to provide more precise spatial information about where radiation propagated from. Employing lenses on an array of single pixel photodetectors 208, such as illustrated in FIG. 5A, may then be able to form an image of a larger area or region of space. Commonly, arrays of single pixel photodetectors 208 are arranged in two dimensional arrays such that a single lens focuses radiation received from a region of space onto the array of photodetectors 208. Using a single lens and a two-dimensional photodetector 208 array, provides two-dimensional spatial information of an area or region, potentially increasing the spatial image resolution of that target area or region of space. Lenses may be implemented, along with other components such as lens tubes, spatial apertures, and device casings, to alter a photodetector's 208 field of view, allowing it to detect radiation from target areas or regions of interest.

One defining characteristic of a lens is the lens's focal length. The focal length of a lens determines how far a target area or region of space must be from the lens for a corresponding photodetector 208 to detect light from or image that object. The corresponding photodetector 208 must be placed at a location relative to the lens that allows the photodetector 208 to receive electromagnetic radiation from the target area or region of space focused on by the lens. As is understood, the field of ray optics may be used to determine the desired position of a photodetector 208 and lens in order to image a target area or region.

In any embodiment the photodetector 208 may be bare photodiodes, lensed or fiber coupled photodiodes, photodiode arrays, photovoltaic sensors, photoresistors, photomultipliers, small button cameras, contact image sensors, or any other device capable of detecting electromagnetic radiation and generating a signal. Depending on the electromagnetic radiation frequencies of interest (e.g. one or more signal fluorescences and one or more reference fluorescences) the photodetector 208 may employ various materials such as silicon, germanium, indium gallium arsenide, lead sulfide, cadmium telluride, copper indium diselenide, cadmium sulfide, indium antominide, or other materials able to convert electromagnetic radiation into a signal. It should be understood that factors in a given embodiment affect the choice of photodetector which may include, without limitation, the wavelengths of fluorescent signals and references, form factor of the photodetector, thickness of the radiation guiding medium, dimensions of a target area or region, desired image resolution, or any other factors.

In embodiments, the photodetector 208 configured to image a fluorescent signal generated by a fluorophore or analyte at or near a portion of the opposing surface 212 of the planar radiation guiding medium 206 may be one or more small button cameras, such as those commonly integrated into mobile devices including smart phones, tablet computers, and the like. Such cameras are very compact and can be designed to have very short focal lengths and large fields of view. Current button cameras may have millions of pixels providing image resolutions in the range of several hundred dots or pixels per inch. High resolutions, such as those provided by button cameras, provide greater spatial detail and information about a target area or region. In an embodiment 400 depicted in FIG. 5A, a button camera array 406 may be disposed on or adjacent to a first planar surface 210 of a planar radiation guiding medium 206. The button cameras in the array 406 may be interlaced with a light source array 402 on or adjacent to the planar radiation guiding medium 206. In this way an array of alternating excitation energy sources 402 and cameras 406 may be able to address individual pixels. Addressing pixels independently may help prevent degradation of a fluorophore and could enable a scalable device able to provide image information of a large target area or region.

Of course, in other embodiments, such as those illustrated in FIGS. 2A-2B and FIGS. 4A-4C, a single button camera photodetector 208 may suffice to capture the fluorescence signal of interest, either because the photodetector 208 has a wide field of view (e.g., wide enough to image all or most of the surface 212) or because the portion of the surface 212 that is of interest is small enough to fit within the field of view of the photodetector 208.

Figure 5B:
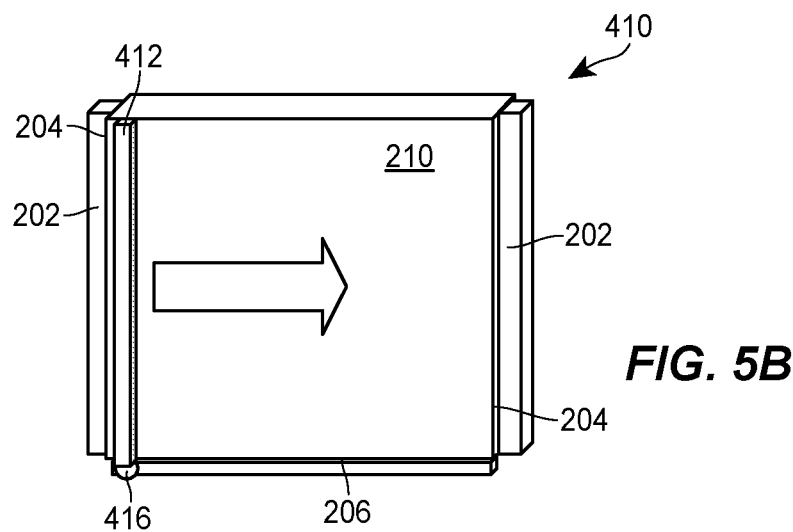
FIG. 5B depicts an embodiment of a compact optode with two excitation radiation sources and a contact image sensor that can be swept along a planar surface of the radiation guiding medium.
Figure 5C:
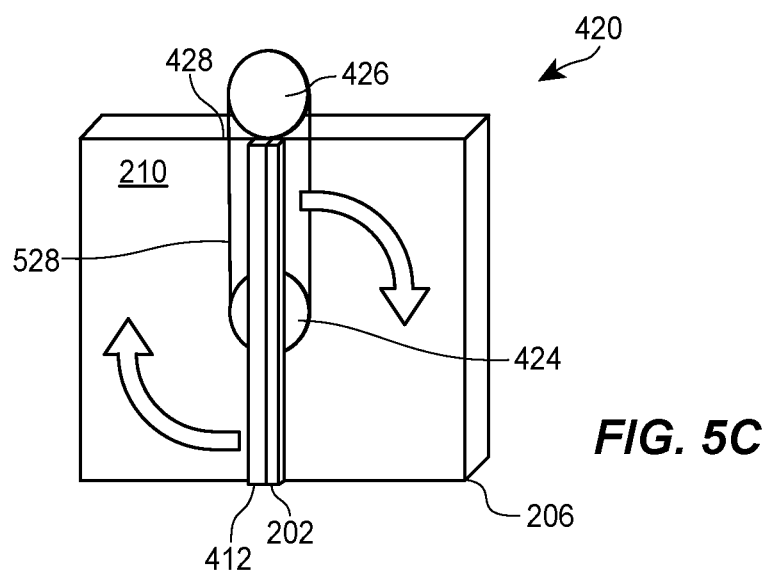
FIG. 5C depicts an embodiment of a compact optode with two excitation radiation sources and a contact image sensor that can be swept radially along a planar surface of the radiation guiding medium.

In still other embodiments, such as those depicted in FIGS. 5B and 5C, the photodetector 208 may be a contact image sensor 412 consisting of a one-dimensional sensor array, such as those used in image scanning peripherals commonly employed with computers or in dedicated scanners and copying machines. In embodiments, the contact image sensor 412 could alternatively be a two-dimensional sensor array. In any event, contact image sensors are compact and can have resolutions greater than 1200 dots or pixels per inch. Typically, an array of small focal length graded index (GRIN) rod lenses are placed in front of the sensor array. The GRIN rod lenses allow the sensors to be distances 10 to 15 millimeters from an object being imaged. FIG. 5B shows one embodiment of an optode 410 using a contact image sensor 412 as the photodetector 208. Excitation energy sources 202 inject excitation energy into the planar radiation guiding medium 206 through perimeter surfaces 204. Because the contact image sensor 412 captures one-dimensional images, a translational motor 416 may be configured to sweep the one-dimensional contact image sensor 412 along a direction perpendicular to the dimension of the contact image sensor 412 along a first planar surface 210 of the planar radiation guiding medium 206. The contact image sensor 412 may capture multiple images as it translates across the first planar surface 210 of the planar radiation guiding medium 206. A processor may then process and patch together the one-dimensional images to provide a two-dimensional image of the opposing planar surface 212 of the planar radiation guiding medium 206.

In another embodiment, a contact image sensor 412 is placed on or affected by a rotating motor 426 or disk 424 as shown in FIG. 5C. The embodiment depicted in FIG. 5C illustrates the contact image sensor 412 mounted on a rotary disk 424. A motor 426 at an edge 428 of the radiation guiding medium 206 rotates the rotary disk 424 by way of a belt 428. Placing the motor 426 at the edge 428 of the radiation guiding medium 206 helps reduce any increase in thickness of the optode device 420 due to an added motor layer. The contact image sensor 412 may take multiple one-dimensional images as it is rotated. Alternatively, the motor 426 may be placed at the point of rotation of the contact image sensor 412 (in place of the rotary disk 424) to rotate the contact image sensor 412. A processor may then process and patch together the one-dimensional images to provide a two-dimensional image of the opposing planar surface 212 of the planar radiation guiding medium 206. In addition, in the embodiment of FIG. 5C, an excitation energy source 202 is mounted alongside the contact image sensor 412. Mounting both the excitation energy source 202 and the contact image sensor 412 on the same rotary disk 424 allows for the illumination of a target area or region of a fluorophore or analyte, instead of illuminating an entire sample. In some embodiments, illuminating only a target area or region may reduce fluorophore degradation increasing the device lifetime and decreasing the frequency of device maintenance. Of course, the excitation energy source 202 could alternatively be mounted on the perimeter surface (s) 204 as described elsewhere in this description.

Figure 6A:
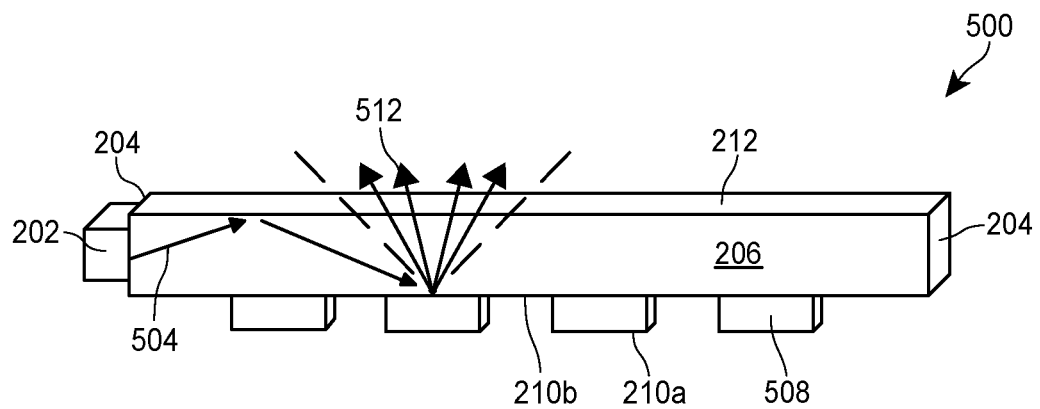
FIG. 6A illustrates a compact optode with a planar radiation guiding medium having an etched or printed radiation extraction pattern.
Figure 6B:
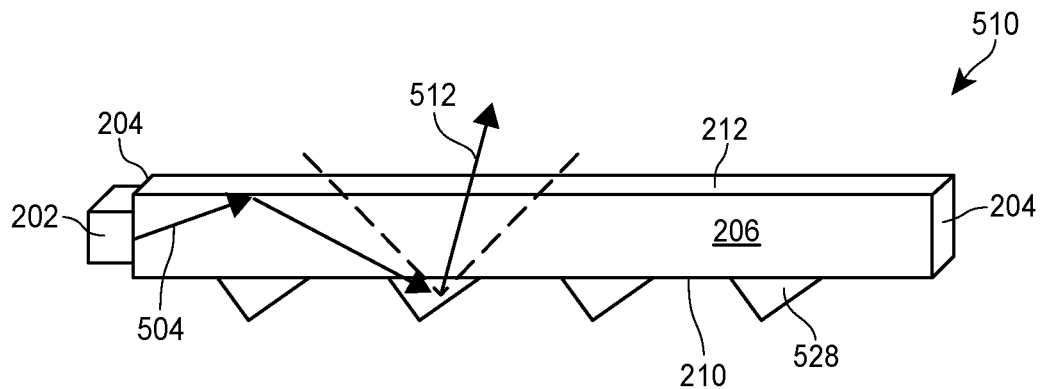
FIG. 6B illustrates a compact optode with a planar radiation guiding medium having a series of prisms on one surface for radiation extraction.
Figure 6C:
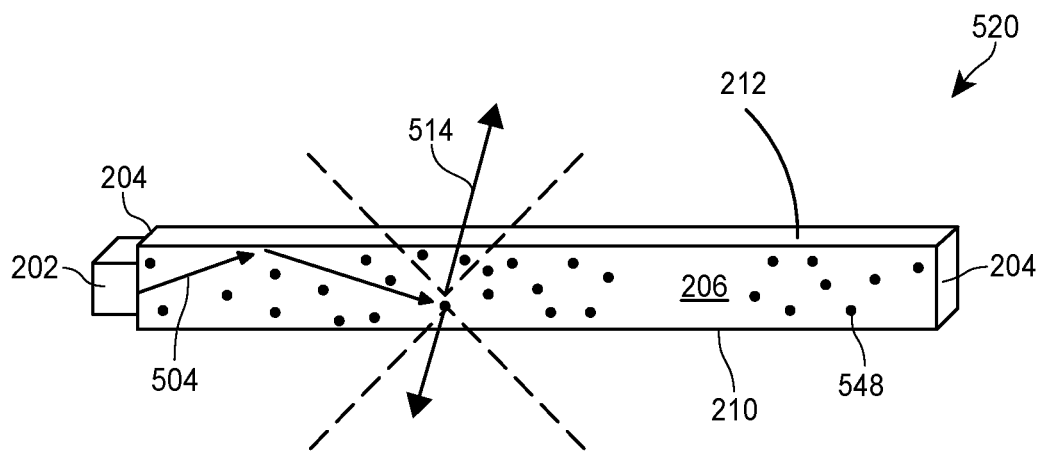
FIG. 6C illustrates of a compact optode with a planar radiation guiding medium having a scattering elements throughout the medium.

In a compact optode device, the planar radiation guiding medium 206 guides the excitation energy in the two-dimensional plane of the radiation guiding medium 206 through total internal reflection, as described with respect to FIG. 3A. Typical planar radiation guiding mediums 206 used for visible frequency bands, guide electromagnetic radiation with efficiencies as high as 85%. Due to the high efficiency of the radiation guiding medium 206 the radiation or excitation energy 214 must be extracted from the planar radiation guiding medium 206 to excite a fluorophore or analyte. FIGS. 6A to 6C depict various methods for achieving extraction of the excitation energy. To prevent leakage at perimeter surfaces 204, some embodiments may employ mirror coatings on the perimeter surfaces 204 where excitation energy 504 is not being injected into the radiation guiding medium 206. For a compact planar optode 200 the perimeter surfaces 204 are not being imaged by the photodetectors 208. Therefore, radiation escaping the radiation guiding medium 206 through the perimeter surfaces 204 decreases the amount of excitation energy delivered to a fluorophore or analyte.

FIGS. 6A-6C depict various physical features that may be used to extract light from the otherwise internally-reflective radiation guiding medium 206. Of course, as will be familiar such physical features are generally very small, with a thickness of sub-millimeter scale and lateral dimensions at the millimeter or sub-millimeter scale. Thus, the features of FIGS. 6A-6C are not to scale but, rather, are depicted out of scale in order to be easily described. FIG. 6A depicts an embodiment 500 in which an excitation source 202 emits excitation energy 504 into a radiation guiding medium 206 through a perimeter surface 204. An excitation energy extraction pattern 508 on the first planar surface 210 of the planar radiation guiding medium 206 reflects the excitation energy 504 at an angle not guided by the radiation guiding medium 206. Reflected excitation energy 512 incident on the opposing planar surface 212 at angles less than the critical angle 214, as illustrated in FIG. 3, of the radiation guiding medium 206 is not guided by the radiation guiding medium 206. At least a portion of the reflected excitation energy 512 passes though the opposing planar surface 212 of the radiation guiding medium 206 where it may enter an area or region with a fluorophore or analyte, while some portion of the reflected excitation energy 512 may be reflected by the opposing planar surface 212 and as a result escape from the first planar surface 210.

While the excitation energy extraction pattern 508 of embodiment 500 is periodic, the excitation energy extraction pattern 508 may also have a graded period or other design as to extract more excitation energy 504 at certain areas or regions than others. The excitation energy extraction pattern 508 also need not be box-like or hyperrectangular, as illustrated in the embodiment 500, but in fact may be any shapes or designs. The excitation energy extraction pattern 508 could be laser etched, chemically etched, or any other method of etching. Etching is a process where material is removed from a surface to generate a pattern or design. Therefore, the raised surface 210a of the extraction pattern 508 is the first planar surface 210 on which the extraction pattern 508 is etched.

The excitation energy extraction pattern 508 could also be printed on the first planar surface 210 of the planar radiation guiding medium 206, where the indented surface 210b is the original surface 210 of the planar radiation guiding medium 206. Etching, printing, or a combination of etching and printing may be preferred for generating the excitation energy extraction pattern 508. Determining a preferred method for generating the excitation energy extraction pattern 508 may depend on the material properties of the radiation guiding medium 206, the size and shape of the radiation guiding medium 206, the required size and resolution of the excitation extraction pattern 508, the complexity of the excitation energy extraction pattern 508, the energies of the excitation energy 504 to be guided and extracted, and/or any other potentially influential factors.

FIG. 6B shows an alternative embodiment 510 in which micro-optical v-grooves 528, or small prisms are attached to or fabricated on a first planar surface 210 of the planar radiation guiding medium 206. As previously mentioned, etching could be used to generate shapes other than box-like hyperrectangles, including the prisms 528 of the embodiment 510 in FIG. 6B. For simplicity we will discuss the excitation energy extraction pattern 528 of embodiment 510 in terms of printing or fabrication on the first planar surface 210. The excitation energy source 202 injects excitation energy 504 into the planar radiation guiding medium 206 through the perimeter surface 204. The micro-optical v-grooves 528 reflect the excitation energy 504 at an angle not guided by the planar radiation guiding medium 206. Some portion of the reflected excitation energy 512 passes though the opposing planar surface 212 of the radiation guiding medium 206 where it may enter an area or region with a fluorophore or analyte.

FIG. 6C shows yet another alternative embodiment 520 in which scattering elements 548 in the volume of the planar radiation guiding medium 206 facilitate the extraction of excitation energy 512 from the planar radiation guiding medium 206. The excitation energy source 202 injects excitation energy 504 into the planar radiation guiding medium 206 through the perimeter surface 204. The scattering elements 548 suppress total internal reflection of the excitation energy 504 in the planar radiation guiding medium 206 resulting in diffuse output of reflected excitation energy 512. The scattered excitation energy 514 passes through the opposing planar surface 212 of the planar radiation guiding medium 206 into at least one area or region with a fluorophore or analyte.

With careful design of the extraction pattern 408, v-grooves 428, or scatterers 448 the excitation energy injected into a perimeter surface 204 by an excitation energy source 202 is able to be uniformly distributed to a fluorophore or analyte, instead of exhibiting a decaying intensity across the plane 212 of the radiation guiding medium 206. To reduce the affect the extraction pattern 408 may have on imaging of the opposing planar surface 212, it is advantageous to place the extraction pattern 408 on or near the first planar surface 210 closer to the photodetector 208. In embodiments 500 and 510 where the extraction patterns 508 and 528 are on the first planar surface 210 closer to the photodetector 208, the extraction patterns 508 and 528 are not imaged by the photodetector 208 because the extraction patterns 508 and 528 are not at or near the focal length of the photodetector 208. The focal length of the photodetector 208 is designed to image the opposing planar surface 212 of the radiation guiding medium 206, and therefore it does not image objects or features on the first planar surface 210 of the radiation guiding medium 206 closer to the photodetector 208

Figure 7A:
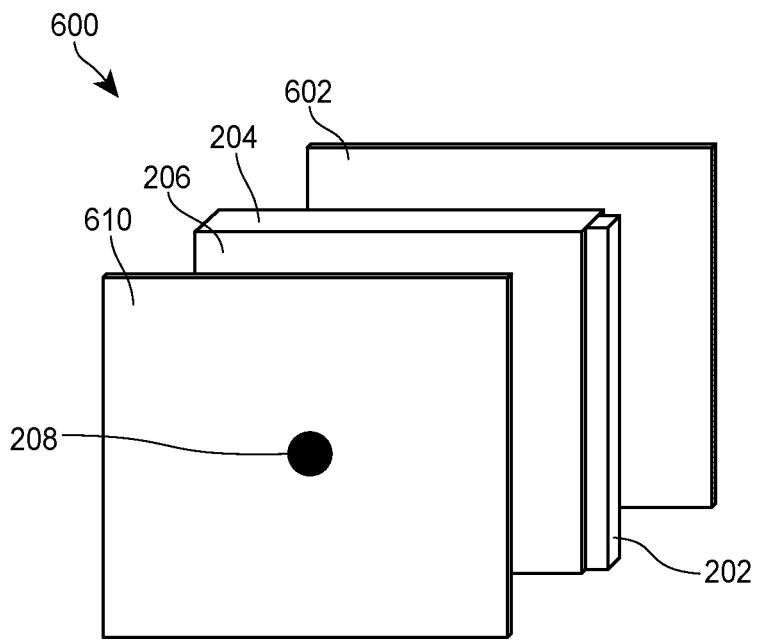
FIG. 7A depicts an embodiment of a compact optode having a protective panel and an optical filter.
Figure 7B:
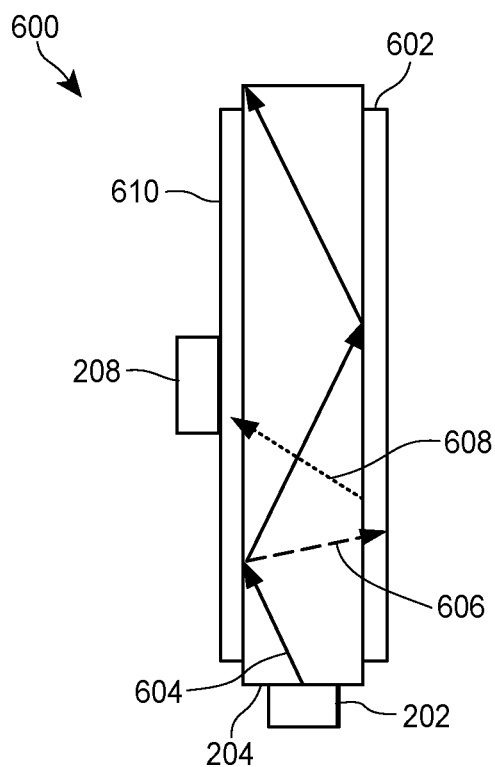
FIG. 7B is a top view of the embodiment in FIG. 6A.

With reference now to FIGS. 7A and 7B, FIG. 7A illustrates an exploded view of an embodiment in which a protective panel 602 is affixed to the second planar surface 212 of the radiation guiding medium 206, while FIG. 7B illustrates a side view of the (unexploded) embodiment of FIG. 7A. The protective panel 602 may have a first side in contact with the second planar surface 212 of the radiation guiding medium 206, and a second side that is exposed to analyte and may include one or more fluorophores. An excitation energy source 202 disposed on a perimeter surface 204 of the planar radiation guiding medium 206 injects excitation energy 604 (solid line) into the radiation guiding medium 206. The protective panel 602 is placed between the planar radiation guiding medium 206 and a sample or analyte of interest. Extracted excitation energy 606 (thick dotted lines) excites a fluorophore on the exposed face of the protective panel 602, which may then fluoresce. A fluorescent signal 608 (fine dotted line) is measured by a photodetector 208. The presence and concentration of an analyte may then be determined from the measured fluorescent signal 608. Fluorophores on the protective panel 602 may be any fluorophore suitable for a given embodiment. It should be understood that factors in a given embodiment affect the choice of fluorophore include, without limitation, the analyte of interest, fluorescence lifetime of the fluorophore, excitation and emission frequencies of the fluorophore, fluorophore resistance to photobleaching, the quantum yield of the fluorophore, the extinction coefficient of the fluorophore, and, in embodiments employing multiple fluorophores, the characteristics of other fluorophores in the embodiment.

In embodiments, the protective panel 602 may have multiple fluorophores multiplexed together that are affected by different analytes. For example, one fluorophore may be affected by a first analyte while a second fluorophore, inert to the first analyte, is affected by a second analyte. In this way multiple analytes may be measured using a single optode 200. In another embodiment, with multiple fluorophores on the protective panel 602, one fluorophore may be sensitive to the analyte while a second fluorophore is inert to any substance or material in the sample. In this way, the second fluorophore may provide a reference fluorescence discussed in further detail below. In embodiments including the protective panel 602, an optical isolation layer may be included on the sample facing side of the protective panel 602 to prevent light from the surrounding environment from entering the optode 200.

In embodiments, a filter 610 may be placed between the planar radiation guiding medium 206 and the photodetector 208. The filter 610 may transmit desired radiation energies while blocking other radiation energies from reaching the photodetector 208. FIG. 7B illustrates a top down view of an embodiment 600 with a protective panel 602 and a filter 610.

As a non-limiting example, excitation energy 604 and a fluorescent signal 608 may be electromagnetic waves or optical energy with wavelengths of 400 nm, and 650 nm, respectively, while the filter 610 may be a pass band filter that transmits optical radiation between 600 and 700 nm, and blocks radiation outside of the 600 to 700 nm wavelength band. The photodetector 208, therefore, would detect the 650-nm fluorescent signal 608, and not the 400-nm excitation energy 604, or any other energy at a wavelength outside of the filter pass band. In other embodiments the filter 610 may be a color filter film, a dichroic mirror, or a grating that accomplishes a similar desired filtering effect.

Color filter films transmit radiation at a band of wavelengths, and absorb radiation at other colors or bands of wavelengths. Therefore, any of the excitation energy incident on the color filter film is absorbed and not delivered to a fluorophore in a sample or the protective panel 602. The color filter film also heats up as it absorbs more excitation energy which may be problematic. Dichroic mirrors, on the other hand, transmit radiation at a band of wavelengths while reflecting radiation at other wavelengths. Due to the reflective nature of dichroic mirrors, embodiments that employ a dichroic mirror as the filter 610 may deliver more excitation energy to a sample or protective panel 602 than an embodiment employing a color filter films the filter 610 given a fixed input excitation energy 604 for both embodiments. In embodiments employing dichroic mirrors, angle tolerances of the mirror must be considered which may cause the transmission band of the dichroic mirror to shift. Although the embodiment 600 depicted in FIGS. 7A and 7B contains both a protective panel 602 and a filter 610, other embodiments may contain a protective panel 602 or a filter 610 independently and need not necessarily include both.

Direct measurements of a fluorescent signal may be affected by factors not directly related to analyte presence and/or concentration. Errors may be introduced by scatterers and absorbers in the radiation guiding medium 206, filters, or any other element of the optode traversed by the fluorescent signal. Scatterers and absorbers between a fluorophore and a photodetector can cause areas to appear darker, even though the actual fluorescence is the same as other detected bright areas. Embodiments implementing one or more reference signals may mitigate the errors associate with intermediate scatterers and absorbers, allowing the optode 200 to more accurately discern the presence and/or concentration of an analyte.

In some embodiments, an excitation energy source 202 may provide excitation energy to one or more fluorophores causing a first and second fluorescence, with the first fluorescence being a fluorescent signal from a fluorophore that may be affected by an analyte, and the second fluorescence being at a same or different energy than the fluorescent signal. The second fluorescence may or may not be affected by the presence of an analyte. In embodiments, the second fluorescence may constitute a fluorescent reference. Such a reference fluorescence may be useful for mapping fluorophore or fluorophore concentrations and determining scattering elements between a fluorophore and a photodetector. Instead of determining the presence and/or concentration of an analyte from the absolute intensity of a fluorescent signal, the fluorescent reference may be subtracted from the fluorescent signal to generate a relative signal fluorescence. Through subtraction of the reference fluorescence, potential measurement errors due to system imperfections such as fluorophore incongruities or scattering elements may be mitigated.

Typically, analyte sensitive fluorophores are used for generating a fluorescent signal and analyte insensitive fluorophores are used for generating the fluorescent reference. Different fluorophores may fluoresce at different wavelengths, for example the fluorescent signal may have a wavelength of 620 nm, in the red band of wavelengths, and the fluorescent reference may have a wavelength of 500 nm, in the green band of wavelengths. In such an embodiment, an LED emitting excitation energy at 450 nm, in the blue band of wavelengths, may be used as the excitation energy source 202 causing both the fluorescent reference and signal to be emitted simultaneously. The photodetector 208 may then capture both the fluorescent reference and signal simultaneously. As discussed above, the photodetector 208 may be multiple narrow-band photodetectors detecting different frequencies, wavelengths, or colors, or wide-band photodetectors able to detect wide bands of electromagnetic radiation. A processor may filter and process the signal or data from the photodetector and may discern the intensities of the signal and reference fluorescences. The signal fluorescence may then be compared to the reference fluorescence to determine errors in analyte measurements due to incongruous fluorophore concentration, scatterers and absorbers in the radiation guiding medium, or other factors that may cause errors in determining the presence and/or concentration of an analyte.

Figure 8A:
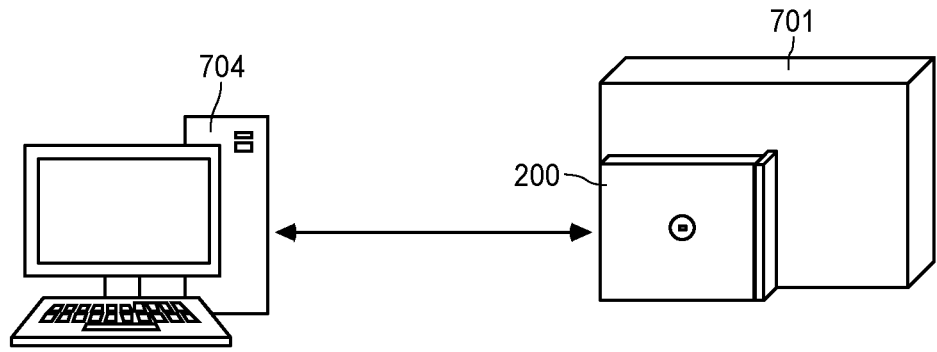
FIG. 8A shows a system wherein a processor is communicatively coupled to a compact optode.

The optode 200, when situated in or adjacent to a sample environment 701, may be communicatively coupled to a computer 700 as illustrated in FIG. 8A. The computer 700 receives signals from the optode 200 in order to process and store data received from the optode 200 and, in embodiments, may also send signals to the optode 200 to control various aspects of the operation of the optode. The optode 200 may be communicatively coupled to the computer 700 by one or more wired or wireless networks 702. In embodiments, a portion of the one or more networks 702 may include the Internet, which may allow for the computer 700 to communicate with a plurality of remote optodes 200 placed at test sites or in the field. In embodiments, the computer 700 may be a local computer 700 for each optode 200, or for a group of optodes 200 that are generally in the same vicinity as the computer 700, and the computer(s) 700 may communicate with one another and/or with another computer (not shown) operative to collect data from the computers 700. In still further embodiments, the computer 700 may be a computer module 700' (rather than the workstation depicted as computer 700 in FIG. 8A) that is attached to or situated with the optode 200 in the sample environment. In these embodiments, the computer module 700' may be configured to control the optode 200 and to process and store locally data captured, either continuously or periodically, from the optode 200 over some period of time. The computer module 700' may, in various embodiments, be retrieved from the optode 200 (e.g., in a modular configuration) and replaced with another computer module 700', or may communicate with another computer (e.g., the computer 700) via a local or wide area network to facilitate retrieval of the data by the computer 700 from the computer module 700'.

Figure 8B:
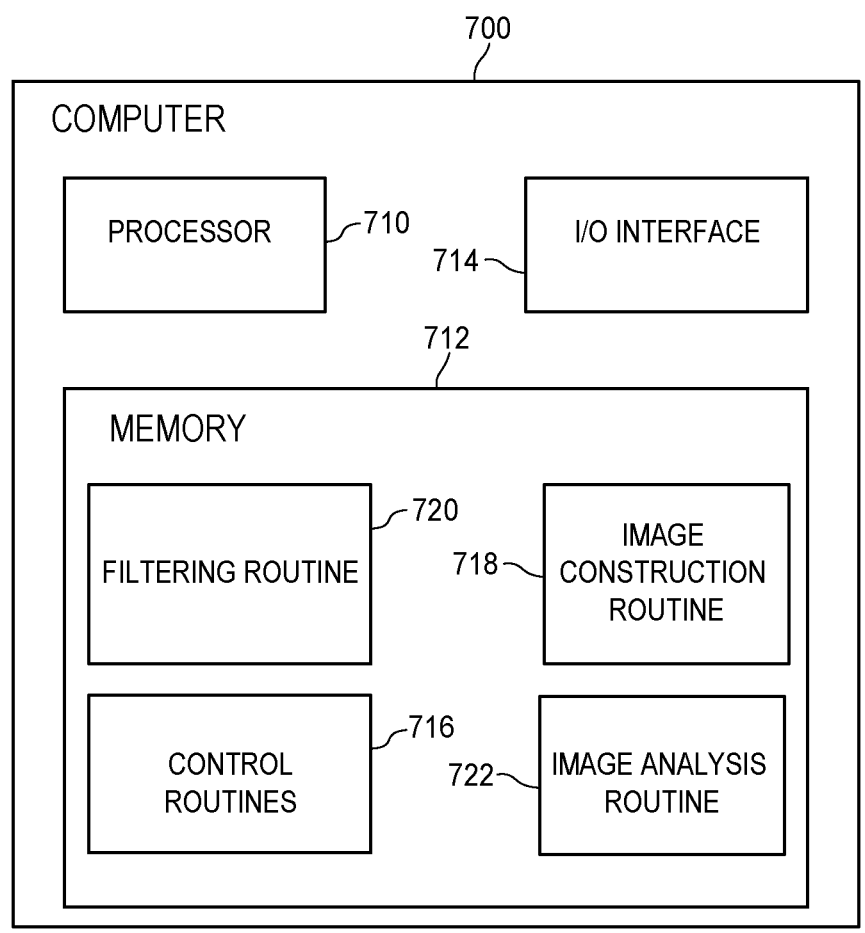
FIG. 8B is a block diagram of an example processor unit communicatively coupled to a compact optode.

FIG. 8B is a block diagram of an example computer 700 (or computer module 700'). The computer 700 includes a processor 710, a memory 712, and an input/output (I/O) interface 714. While described herein as a single processor 710, the processor 710 may be multiple processors operating in parallel in some embodiments. Additionally, the processor 710 may be a general purpose processor specifically configured to perform the various routines associated with the optode 200 and described below, or may be a special purpose processor (e.g., a field-programmable gate array, digital signal processor, graphics processing unit, application specific integrated circuit, etc.) designed and/or configured to perform the various routines associated with the optode 200 and described below. The memory 712 may be a volatile memory, a non-volatile memory, or some combination of volatile and non-volatile memory, and may include a single storage device or multiple storage devices, as is generally understood. The memory device 712 may store raw data received and/or retrieved from the optode 200 (and specifically from the photodetector 208), may store processed data (e.g., data that have been filtered, combined, analyzed, etc.), may store routines for execution by the processor 710, and may store an operating system or other routines for operation of the computer 700.

In embodiments, the memory 712 stores (and the processor 710 may be configured according to) machine-executable instructions (referred to as "routines," "modules," "programs," etc.) that, when executed by the processor 710 cause the processor 710 to perform various actions for control of the optode 200 and/or analysis of data received or retrieved from the optode 200 and, in particular, from the photodetector 208. In embodiments, one or more control routines 716 executed by the processor 710 may cause the processor 710 to send control signals to the optode 200 via the I/O interface 714. The control routines 716 may control the operation of the excitation energy source 202, controlling, in various embodiments, whether the excitation energy source 202 is on or off, the intensity of the excitation energy source 202, synchronization of the excitation energy source 202 with the data collection of the photodetector 208 and, in embodiments in which there are multiple excitation energy sources 202, which of the multiple excitation energy sources 202 is energized at any given time. The control routines 716 may also control the photodetector 208, causing the capture of detected fluorescent signals and/or references at various times and/or by various ones of multiple photodetectors (e.g., photodetectors in an array, photodetectors configured for different wavelengths, etc.), and to store the captured data in the memory 712. Still further, in embodiments implementing a 1D contact image sensor 412 as the photodetector 208, the control routines 716 may control a motor that translates or rotates the contact image sensor to capture data of a fluorescent signal and/or reference.

The memory 712 may also store an image construction routine 718 that, when executed by the processor 710, causes the processor 710 to put together data from multiple photodetectors 208 to form a single image. For instance, the image construction routine 718 may assemble into a single image the data received from a multitude of discrete photodetector components arranged in a 1D or 2D array, may assemble into a single image the data received from multiple camera elements (e.g., button cameras), each of which is an array of photodetectors in its own right, may assemble into a single image the data received from an array of photodetectors making up a contact image sensor 412, the data received as the contact image sensor 412 is translated or rotated, etc.

The memory 712 may also store, in embodiments requiring it, one or more image filtering routines 720. The image filtering routines 720, when executed by the processor 710, cause the processor 710 to perform various filtering of the data received from the photodetector 208. The filtering can include color filtering, sharpening and unsharpening masks, local averaging, or any other form of image filtering. Generally, however, the filtering will include filtering to remove from the data received from the photodetector 208 any of the excitation energy that may have been captured by the photodetector 208, to remove from the data one or more wavelengths of fluorescent data (e.g., to remove the reference fluorescence data to view the signal fluorescence data, to remove the signal fluorescence data to view the reference fluorescence data, etc.), to remove noise (e.g., ambient light) from the signal, and/or to remove portions of the signal below or above a desired intensity. The data output from the filtering routine 720 may be stored with, or may replace, the raw data received from the photodetector 208 and/or the data output from the image construction routine 718.

An image analysis routine 722, when executed by the processor 710, may cause the processor 710 to perform various image analyses on the raw image data, the constructed image data, and/or the filtered image data to determine the presence and/or concentration of an analyte in the sample environment 701. In an embodiment, the image analysis routine 722 may receive image data from the image processing unit 718, or retrieve image data from the memory 712, and may store the resultant analyte presence and/or concentration information in the memory 712, or send the information via the I/O interface 714 to other processing units, memories, networks, displays, or any other device. In embodiments, the image analysis routine 722 may cause the processor 710 to analyze an image representing a reference fluorescence and/or may compare the reference fluorescence data with a signal fluorescence data to normalize the signal fluorescence data and to compensate for the properties of the fluorophore distribution, the planar radiation guiding medium 206, etc. The image analysis routine 722 may also cause the processor 710 to compare current data with previous data, to compare a fluorescent signal to a threshold, and the like.

Figure 9:
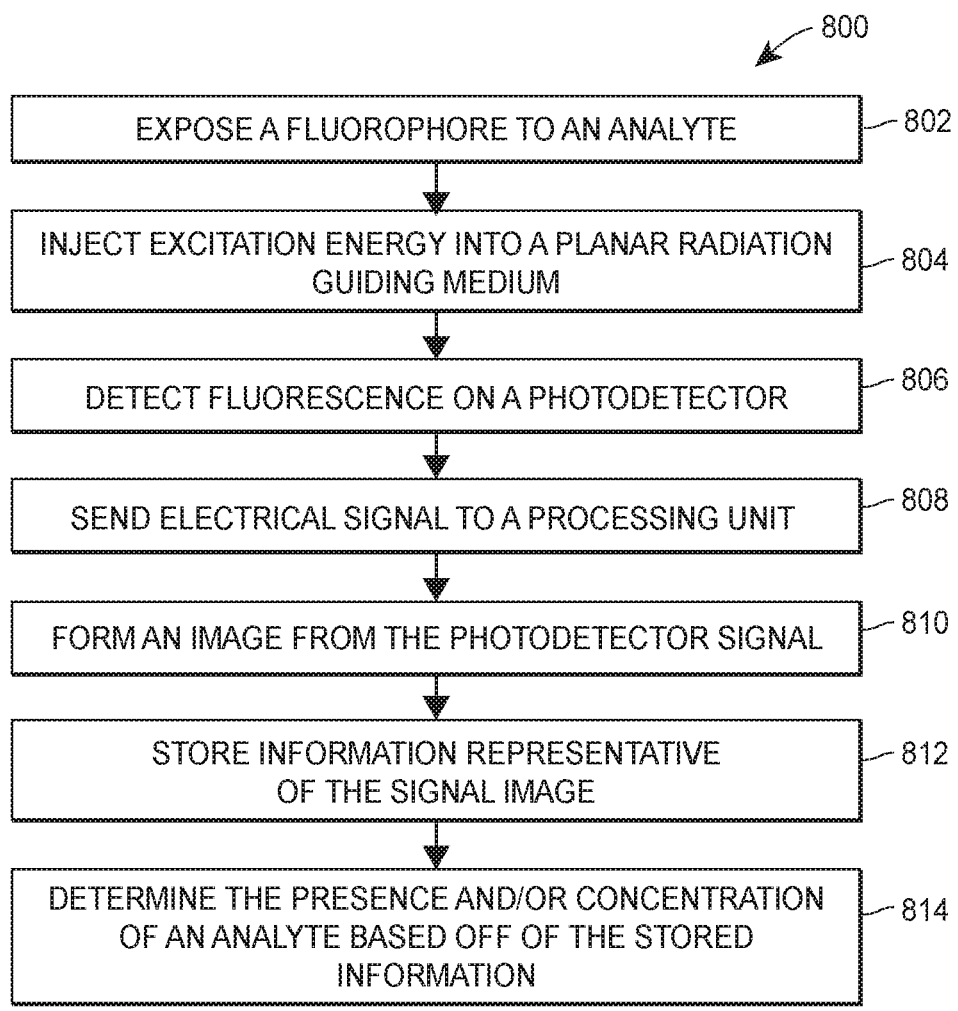
FIG. 9 is a flow chart of a method for determining the presence and/or concentration of an analyte using a compact optode.

FIG. 9 is a flow diagram showing an example method 800 for determining the presence and/or concentration of an analyte and, in particular, a method that could be performed by the optode embodiment 600 of FIG. 7A. A fluorophore is exposed to an analyte (block 802). The fluorophore may be on the protective panel 603 in contact with a sample, in embodiments. The protective panel separates the radiation guiding medium from the environment to prevent dirt or other scatterers from falling onto the radiation guiding medium surface and destroying the total internal reflection condition. In other embodiments the fluorophore may be diluted in the sample containing an analyte. Other embodiments may employ any other method to expose a fluorophore to an analyte. In any event, an excitation energy source 202 injects excitation energy 604 into a planar radiation guiding medium 206 (block 804). Extracted excitation energy 606 passes through an opposing planar surface 212 of the planar radiation guiding medium 206 and excites a fluorophore or analyte which may cause it to fluoresce. A photodetector 208 detects fluorescence (block 806) and the photodetector 208 sends an electrical signal to a processing unit 704 (block 808) communicatively coupled to the photodetector 208. The processing unit 704 may perform image filtering, image stitching, or other processing routines to form an image from the photodetector signal (block 810). Information and data representative of the signal image is stored in one or more memories 712 (block 812). The presence and/or concentration of an analyte is determined from the stored information (block 814). The method 800 may be performed by an optode disclosed in the embodiments described herein or another optode device.

The following list of aspects reflects a variety of the embodiments explicitly contemplated by the present disclosure. Those of ordinary skill in the art will readily appreciate that the aspects below are neither limiting of the embodiments disclosed herein, nor exhaustive of all of the embodiments conceivable from the disclosure above, but are instead meant to be exemplary in nature.

1. An optode comprising: a planar radiation guiding medium having a first planar surface and a second planar surface and one or more perimeter surfaces bounded by the first and second planar surfaces; an excitation energy source configured to output into the radiation guiding medium first energy at a wavelength selected to excite a fluorophore; and a photodetector configured to image at least a portion of the first planar surface of the radiation guiding medium by detecting second energy transmitted through the radiation guiding medium.

2. An optode according to aspect 1, further comprising a protective panel affixed to the first planar surface of the radiation guiding medium, the protective panel having a first surface in contact with the first planar surface of the radiation guiding medium and a second surface exposed to an analyte.

3. An optode according to aspect 2, wherein the second surface of the protective panel includes a first fluorophore sensitive to the analyte.

4. An optode according to aspect 3, wherein the second surface of the protective panel further comprises a second fluorophore.

5. An optode according to aspect 4, wherein the second fluorophore is insensitive to the analyte.

6. An optode according to any one of aspects 1 to 5, wherein the radiation guiding medium comprises an extraction pattern on the first planar surface, the second planar surface, or both the first and second planar surfaces.

7. An optode according to aspect 6, wherein the extraction pattern is printed on the radiation guiding medium.

8. An optode according to aspect 6, wherein the extraction pattern is chemically etched on the radiation guiding medium.

9. An optode according to aspect 6, wherein the extraction pattern is laser etched on the radiation guiding medium.

10. An optode according to aspect 6, wherein the extraction pattern comprises an array of prisms formed on the radiation guiding medium.

11. An optode according to any one of aspects 1 to 5, wherein the radiation guiding medium comprises scattering elements throughout the volume radiation guiding medium.

12. An optode according to any one of aspects 1 to 11, wherein the excitation energy source comprises a plurality of light emitting diodes (LEDs).

13. An optode according to aspect 12, wherein the plurality of LEDs forms an array of LEDs.

14. An optode according to aspect 12, wherein the plurality of LEDs forms two arrays of LEDs.

15. An optode according to any one of aspects 12 to 14, wherein an array of LEDs is disposed along the perimeter surface of the radiation guiding medium.

16. An optode according to any one of aspects 12 to 14, wherein two arrays of LEDs are disposed along opposite portions of the perimeter surface of the radiation guiding medium.

17. An optode according to aspect 13, wherein the array of LEDs is disposed on the second planar surface of the radiation guiding medium.

18. An optode according to any one of aspects 1 to 11, wherein each of the first and second planar surfaces of the radiation guiding medium is a parallelogram, wherein the excitation energy source comprises a plurality of light emitting diodes (LEDs) forming two arrays of LEDs, and wherein the two arrays are LEDs are placed on opposing perimeter surfaces of the radiation guiding medium.

19. An optode according to any one of aspects 1 to 11, wherein the excitation energy source comprises a laser.

20. An optode according to any one of aspects 1 to 19, wherein the wavelength selected is between 400 and 500 nm, inclusive.

21. An optode according to any one of aspects 1 to 19, wherein the wavelength selected is between 450 and 490 nm, inclusive.

22. An optode according to any one of aspects 1 to 11, wherein the excitation energy source comprises a black body source.

23. An optode according to any one of aspects 1 to 22, wherein the photodetector comprises a plurality of mini-cameras disposed as an array on the second planar surface of the radiation guiding medium, such that the portion of the first planar surface is imaged, collectively, by the plurality of mini-cameras.

24. An optode according to any one of aspects 1 to 22, wherein the photodetector comprises a mini-camera disposed on the second planar surface of the radiation guiding medium, such that the portion of the first planar surface is imaged by the mini-camera.

25. An optode according to any one of aspects 1 to 22, wherein the photodetector comprises a contact image sensor (CIS).

26. An optode according to aspect 25, wherein the CIS is translated in one dimension across the second planar surface of the radiation guiding medium.

27. An optode according to aspect 25, wherein the CIS is rotated along the second planar surface of the radiation guiding medium.

28. An optode according to aspect 25, wherein the CIS is a two-dimensional array of sensing elements disposed on the second planar surface of the radiation guiding medium.

29. An optode according to any one of aspects 25 to 27, wherein the excitation energy source is attached to the CIS.

30. An optode according to any one of aspects 1 to 29, further comprising a filter layer disposed on the second planar surface of the radiation guiding medium.

31. An optode according to aspect 30, wherein the filter layer comprises a color filter film.

32. An optode according to aspect 30, wherein the filter layer comprises a dichroic mirror.

33. An optode according to any one of aspects 1 to 32, wherein the fluorophore is selected to emit as the second energy fluorescence in response to the presence of any one or more of: gaseous oxygen ($O_2$), gaseous carbon dioxide ($CO_2$), acidity, deoxyribonucleic acid (DNA), ribonucleic acid (RNA), an organic molecule, an inorganic molecule, and a pathogen.

34. A system comprising: an optode according to any one of aspects 1 to 33, further comprising a processor communicatively coupled to the photodetector and configured to receive from the photodetector a signal representing the detected second energy and to analyze the received signal to determine the presence and/or concentration of an analyte.

35. A system comprising: a planar radiation guiding medium having a first planar surface and a second planar surface and one or more perimeter surfaces bounded by the first and second planar surfaces; an excitation energy source configured to output into the radiation guiding medium first energy at a wavelength selected to excite a fluorophore; a photodetector configured to image at least a portion of the first planar surface of the radiation guiding medium by detecting second energy transmitted through the radiation guiding medium; a processor communicatively coupled to the photodetector and configured to receive from the photodetector a signal representing the detected second energy and to analyze the received signal to determine the presence and/or concentration of an analyte.

36. A system according to aspect 35, wherein the photodetector comprises a plurality of button cameras, and wherein the processor is further configured to perform image processing to assemble an image from the plurality of button cameras.

37. A system according to aspect 35, wherein the photodetector comprises a contact image sensor (CIS), and wherein the processor is further configured to perform image processing to assemble an image from the CIS.

38. A system according to aspect 37, wherein the CIS is translated or rotated by a motor, and wherein the processor is further configured to control the motor.

39. A system according to aspect 37 or aspect 38, wherein the excitation energy source is coupled to the CIS, and wherein the processor is further configured to synchronize illumination by the excitation energy source and capturing of data by the CIS.

40. A system according to any one of aspects 35 to 39, wherein the processor is further configured to execute one or more digital filtering routines.

41. A system according to aspect 40, wherein the one or more digital filtering routines comprise a routine for removing a signal corresponding to the excitation energy source.

42. A system according to aspect 40 or aspect 41, wherein the one or more digital filtering routines comprise a routine for removing a signal corresponding to a reference fluorescence.

43. A system according to any one of aspects 40 to 42, wherein the one or more digital filtering routines comprise a routine for removing a signal corresponding to the detected second energy.

44. A system according to any one of aspects 35 to 43, wherein the excitation energy source is pulsed, and wherein the processor is further configured to synchronize pulsation of the excitation energy source with the detection of the second energy.

45. A system according to any one of aspects 35 to 44, wherein analyzing the received signal to determine the presence and/or concentration of an analyte comprises calculating a ratio relating quantities corresponding to two of the group consisting of: intensity of fluorescence of a first fluorophore responsive to the analyte, intensity of fluorescence of a second fluorophore differently responsive to the analyte than the first fluorophore, intensity of fluorescence of a fluorophore not responsive to the analyte, intensity of the first energy when the second energy is detected, and intensity of the first energy during a reference detection.

46. A system according to any one of aspects 35 to 45 and including the optode of any one of aspects 1 to 34.

47. A method comprising: providing an excitation energy source configured to provide excitation energy of a wavelength selected to excite a fluorophore, the fluorophore selected to fluoresce in the presence of an analyte of interest; exposing the fluorophore to the analyte of interest; injecting into the planar radiation guiding medium the excitation energy; detecting second energy transmitted through the radiation guiding medium to form a signal image of at least the portion of the first planar surface of the radiation guiding medium; storing information representative of the signal image; and analyzing the stored information representative of the signal image to determine the presence and/or concentration of the analyte of interest.

48. A method according to aspect 47, further comprising: injecting into a planar radiation guiding medium reference energy from the excitation energy source, the planar radiation guiding medium having a first planar surface, a second planar surface, and one or more perimeter surfaces bounded by the first and second planar surfaces; detecting a signal from the injected reference energy, at a plurality of points on the first planar surface of the radiation guiding medium, in the absence of the analyte of interest, so as to form a reference image of at least a portion of the first planar surface of the radiation guiding medium; storing information representative of the reference image; comparing the stored information representative of the signal image to the stored information representative of the reference image to determine the presence and/or concentration of the analyte of interest.

49. A method according to either aspect 47 or 48 performed using the optode of any one of aspects 1 to 34 or the system of any one of aspects 35 to 46.

The invention claimed is:

1. An optode comprising:
a planar waveguide element having a first planar surface and a second planar surface and one or more perimeter surfaces bounded by the first and second planar surfaces;
an excitation energy source configured to output into the waveguide element first energy at a wavelength selected to excite a fluorophore;
a one-dimensional contact image sensor array disposed adjacent to the second planar surface of the waveguide element, the one-dimensional contact image sensor array configured to image a plurality of one-dimensional portions of the first planar surface of the waveguide element by detecting second energy transmitted through the waveguide element; and
a processor communicatively coupled to the contact image sensor and configured to:
receive from the contact image sensor a plurality of signals representing the images of the plurality of one-dimensional portions of the first planar surface;
perform image processing to assemble a two-dimensional image from the plurality of one-dimensional images; and
analyze the two-dimensional image to determine the presence and distribution of an analyte in an environment.

2. An optode according to claim 1, further comprising a protective panel affixed to the first planar surface of the waveguide element, the protective panel having a first surface in contact with the first planar surface of the waveguide element and a second surface exposed to an analyte.

3. An optode according to claim 2, wherein the second surface of the protective panel includes a first fluorophore sensitive to the analyte.

4. An optode according to claim 3, wherein the second surface of the protective panel further comprises a second fluorophore.

5. An optode according to claim 4, wherein the second fluorophore is insensitive to the analyte.

6. An optode according to claim 1, wherein the waveguide element comprises an extraction pattern on the first planar surface, the second planar surface, or both the first and second planar surfaces.

7. An optode according to claim 1, wherein the excitation energy source comprises a plurality of light emitting diodes (LEDs).

8. An optode according to claim 7, wherein an array of LEDs is disposed along the perimeter surface of the waveguide element.

9. An optode according to claim 1, wherein the fluorophore is selected to emit as the second energy fluorescence in response to the presence of any one or more of: gaseous oxygen ($O_2$), gaseous carbon dioxide ($CO_2$), acidity, deoxyribonucleic acid (DNA), ribonucleic acid (RNA), an organic molecule, an inorganic molecule, and a pathogen.

10. An optode according to claim 1, further comprising one or more graded index lenses configured to focus the second energy onto the contact image sensor.

11. An optode according to claim 1, wherein the contact image sensor is positioned less than 15 millimeters from the first planar surface.

12. An optode according to claim 2, further comprising an optical isolation layer on the protective panel configured to prevent light from entering the optode through the protective panel.

13. An optode according to claim 1, wherein the optode is configured to detect a gaseous, liquid, or solid analyte in the environment, and wherein the environment is one of air, soil, and water.

14. An optode according to claim 1, wherein the waveguide element is configured to uniformly distribute the first energy to the fluorophore.

15. A system comprising:
a planar waveguide element having a first planar surface and a second planar surface and one or more perimeter surfaces bounded by the first and second planar surfaces;
an excitation energy source configured to output into the waveguide element first energy at a wavelength selected to excite a fluorophore;
a one-dimensional contact image sensor array disposed adjacent to the second planar surface of the waveguide element, the one-dimensional contact image sensor array configured to image a plurality of one-dimensional portions of the first planar surface of the waveguide element by detecting second energy transmitted through the waveguide element; and
a processor communicatively coupled to the contact image sensor (CIS) and configured to:
receive from the contact image sensor a plurality of signals representing the images of the plurality of one-dimensional portions of the first planar surface;
perform image processing to assemble a two-dimensional image from the plurality of one-dimensional images; and
analyze the two-dimensional image to determine the presence and distribution of an analyte in an environment, and wherein the excitation energy source is coupled to the CIS, and wherein the processor is further configured to synchronize illumination by the excitation energy source and capturing of data by the CIS.

16. A system according to claim 15, wherein the CIS is translated or rotated by a motor, and wherein the processor is further configured to control the motor.

17. A system according to claim 15, wherein the processor is further configured to execute one or more digital filtering routines.

18. A system according to claim 15, wherein analyzing the received signal to determine the presence and/or concentration of an analyte comprises calculating a ratio relating quantities corresponding to two of the group consisting of: intensity of fluorescence of a first fluorophore responsive to the analyte, intensity of fluorescence of a second fluorophore differently responsive to the analyte than the first fluorophore, intensity of fluorescence of a fluorophore not responsive to the analyte, intensity of the first energy when the second energy is detected, and intensity of the first energy during a reference detection.

19. A system according to claim 15, wherein the contact image sensor is positioned less than 15 millimeters from the first planar surface.

20. A system according to claim 15, further comprising:
- a protective panel affixed to the first planar surface of the waveguide element, the protective panel having a first surface in contact with the first planar surface of the waveguide element and a second surface exposed to an analyte; and
- an optical isolation layer on the protective panel configured to prevent light from entering the optode through the protective panel.

* * * * *

UNITED STATES PATENT AND TRADEMARK OFFICE
CERTIFICATE OF CORRECTION

PATENT NO.       : 11,035,794 B2
APPLICATION NO.  : 16/146360
DATED            : June 15, 2021
INVENTOR(S)      : Xufeng Zhang et al.

Page 1 of 1

It is certified that error appears in the above-identified patent and that said Letters Patent is hereby corrected as shown below:

On the Title Page

At item (71), Line 4, "THE MARING BIOLOGICAL LABORATORY," should be -- THE MARINE BIOLOGICAL LABORATORY, --.

Signed and Sealed this
Twenty-sixth Day of April, 2022

Katherine Kelly Vidal
*Director of the United States Patent and Trademark Office*